United States Patent [19]
Prewett et al.

[11] Patent Number: 5,507,810
[45] Date of Patent: Apr. 16, 1996

[54] PROCESSING OF FIBROUS CONNECTIVE TISSUE

[75] Inventors: Annamarie B. Prewett, Little Silver; Robert K. O'Leary, Spring Lake, both of N.J.

[73] Assignee: Osteotech, Inc., Shrewsbury, N.J.

[21] Appl. No.: 995,940

[22] Filed: Dec. 21, 1992

Related U.S. Application Data

[63] Continuation of Ser. No. 773,023, Oct. 7, 1991, abandoned.

[51] Int. Cl.$^6$ ............................. A61F 2/64; A61K 35/22
[52] U.S. Cl. .......................... 623/11; 424/422; 623/16; 623/66; 623/13
[58] Field of Search ....................... 623/11, 13, 901, 623/66; 424/422, 423

[56] References Cited

U.S. PATENT DOCUMENTS

| | | | |
|---|---|---|---|
| 4,642,120 | 2/1987 | Nevo et al. | 623/11 |
| 4,801,299 | 1/1989 | Brendel et al. | |
| 4,879,135 | 11/1989 | Greco et al. | 623/11 X |
| 4,946,792 | 8/1990 | O'Leary . | |
| 4,976,733 | 12/1990 | Giradot | 427/2 X |
| 5,067,962 | 11/1991 | Campbell et al. | 623/13 |

FOREIGN PATENT DOCUMENTS 0305026  3/1988  European Pat. Off. .

OTHER PUBLICATIONS

Cameron, J., et al.: Freeze Dried Composite Tendon Allografts: An Experimental Study. Plastic Reconstr. Surg., 47:39–46, 1971.

Urist, M., et al.: A Chemosterilized Antigen Extracted Autodigested Allo–implant for Bone Banks. Arch. Surg., 10:416–428, 1975.

Minami, A., et al.: Effect of the Immunological Antigenicity of the Allogeneic Tendons of Tendon Grafting. Hand, 14:111–119, 1982.

Tauro, J. C., et al.: Comparison of Antigen Extracted, Lyophylized and Glutaraldehyde Fixed Bovine Xenograft. Trans. Soc. Biomat., 7:257, 1984.

Salgaller, M. L., and Bajpai, P. K.: Immunogencity of Glutaraldehyde Treated bovine Pericarial Tissue Xenografts in Rabbits. J. Biomed. Mater. Res., 19:1–12, 1985.

Wilson, A., et al.: The Effect of Extraction and Storage Techniques on Mechanical and Histological Properties of bovine Tendon. Trans. Soc. Biomat., 8:193, 1985.

Tauro, J. C., et al.: Comparison of Untreated and Processed Bovine Tendon Xenografts to Autogenous Grafts. Trans. Soc. Biomater., 10:223, 1987.

Okumura, M.: Effect of Several Enhancers on the Skin Permeation of Water–Soluble Drugs. Chem. Pharm. Bull., 37:1375–1378, 1989.

Kreis, K., et al.: The Use of Non–viable Glycerol–Preserved Cadaver Skin Combined with Widely Expanded Autografts in the Treatment of Extensive Third–degree Burns. J. Trauma, 29:51–54, 1989.

Kai, T. et al.: Mechanism of Percutaneous Penetration Enhancement Effect of n–Alkanols on the Permeability Barrier of Hairless Mouse Skin. J. Controlled Release, 12:103–112, 1990.

Hori, M., et al.: Classification of Percutaneous Penetration Enhancers: A Conceptual Diagram. J. Pharm. Pharmacol., 42:71–72, 1990.

Tauro, J. C. Parsons, J. R., Ricci, J. L. and Alexander, H.: Comparison of Bovine Collagen Xenografts to Autogenous Graft in the Rabbit. Clin. Orthop., 266:271–284, 1991.

*Primary Examiner*—David J. Isabella
*Attorney, Agent, or Firm*—Dilworth & Barrese

[57] ABSTRACT

Fibrous connective tissue for surgical implantation is made substantially antigen-free by contact with one or more extraction agents. Solutions or mixtures of molecules having bipolar regions act as antigen removing permeation enhancers. Cationic, anionic, non-ionic or amphoteric surfactants are suitable bipolar permeation enhancers. One or more extraction agents can be combined to form extraction mixtures.

29 Claims, No Drawings

PROCESSING OF FIBROUS CONNECTIVE TISSUE

This is a continuation of application Ser. No. 07/773,023 filed on Oct. 7, 1991, now abandoned.

FIELD OF THE INVENTION

This invention relates to the processing of fibrous connective tissue for surgical implantation into mammals and more particularly to a process for reducing the immunogenicity and irritability of the implantable tissue.

BACKGROUND OF THE INVENTION

Ligaments consist of bands of various forms, serving to connect together the articular extremities of bones, and are composed mainly of bundles of white fibrous tissue placed in parallel or closely interlaced with one another. A ligament is pliant and flexible, so as to allow freedom of movement, but strong, tough, and inextensile so as not to readily yield under severe force. Consequently, ligaments are well adapted to serve as the connecting medium between bones.

Tendons are white, glistening, fibrous cords, varying in length and thickness, of considerable strength, and devoid of elasticity. They are composed of white fibrous tissue, the fibrils of which have an undulating course parallel with each other and are firmly united together. Tendons are connected between muscles and movable structures such as bones, cartilages, ligaments and fibrous membranes.

The surgical treatment of tendon and ligament injuries is a significant therapeutic problem. Such injury can be profoundly disabling if left untreated. For example, it is well known that athletes' careers are often compromised or even terminated by injury to the cruciate ligaments of the knee. Even in non-athletes, injury to ligaments or tendons may affect any activity where walking or stair climbing is involved. Clinical evidence suggests that chronic instability from ligament damage results in early degenerative joint disease. Surgical reconstruction may be the best way of alleviating symptoms and preventing progressive long term damage. Although various remedial procedures have been developed, there is an unacceptably high incidence of fair or poor results.

Early reconstructive procedures for the cruciate deficient knee focused on manipulation of extra-articular (occurring outside of the joint) tissue to compensate for the loss of intra-articular cruciate. More recently, intraarticular repairs using tissues arising, transferred or transplanted within an individual, i.e., autogenous or autologous structure, have been employed.

The success of surgical reconstruction of damaged tendon or ligament tissue relies on the utilization of appropriate graft material. Optimally, such material should duplicate the original physiological function of the damaged tissue, be biocompatible, readily available, easy to implant, amenable to long term storage, free of transmittable disease and non-immunogenic.

Autologous tissue, including fascia lata, semitendinosus, patella tendon, and tissue from the iliotibial band, is one source of graft material presently employed in the reconstructive surgery of damaged connective tissue. Since the grafting material is taken from the patient, there is no risk of rejection. Although these autografts serve as good replacements, they are not without drawbacks. The limited supply of useable autogenic material is a major disadvantage. Moreover, considerable post-operative morbidity is related to dissection and sacrifice of host tissue, leaving the dissected tissue weaker than undisturbed tissues. Success rates are extremely variable both in the short term and after several years when many of the grafts elongate and result in recurrent instability.

There is a clear need for a non-autologous, readily available graft material which is mechanically adequate in both the long and short term. Short term success with such a graft is dependent upon biocompatibility, initial graft mechanical strength and the ability of the surgeon to implant the graft correctly with minimal post-operative trauma. For a graft to maintain stability in the long-term, it must be well-incorporated by the host and gradually remodeled into a structure with properties similar to the damaged tissue being replaced. Incorporation and remodeling usually involve, among other things, repopulation of the implant with the recipient's fibroblasts and some degree of revascularization.

Synthetic materials such as Goretex® have been developed as a substitute for connective tissue, but have shortcomings. Although synthetics are non-antigenic, constant wear may render them non-biocompatible due to host foreign body responses to wear debris. Moreover, mechanical mismatch between the synthetic material and the host may lead to failure of the implant. Finally, synthetics may not be well-incorporated into the recipient, i.e., they may not be repopulated by host fibroblasts, revascularized, or otherwise incorporated by the host tissues.

Allograft material, i.e., a graft of tissue between individuals of the same species but of disparate genotype, has also been employed, but may exhibit certain disadvantages. The supply of allograft material, like autologous tissue, is limited. There are also increasing concerns regarding viral contamination of allografts, whose viral progeny may ultimately proliferate and infect the recipient of the graft. A third drawback is the alloreactivity of allograft material. Indeed, hyperarcuate rejection can sometimes occur just hours after transplantation and is likely to be due to preformed antibodies to the graft antigens. Acute rejection represents the most commonly treated rejection event. Although many immunosuppressive agents are used to reduce alloreactivity, they can have serious side effects such as lowering the host's resistance to infection. One method being used to decrease the alloreactivity of allograft involves freezing or lyophilization of the allograft.

Xenograft materials, i.e., a graft of material transplanted between animals of different species, are readily available but are potentially the most antigenic and immunogenic of all implantable substitutes.

Reduction of the immunogenicity and/or antigenicity of xenografts as well as any other implant material is desirable because the shortage of suitable implantable tissue would be reduced or alleviated. For example, the supply of replacement tissue would be increased tremendously if bovine tendons and ligaments were used as substitutes for human tendons and ligaments. Fresh tendon allografts or xenografts elicit a potent immune response, stimulating cytotoxic antibodies and cell-mediated immunity. The rejection response ie due to cellular antigens and not the collagen matrix which serves as the tissue's backbone structure. Consequently, removal or blockage of cellular antigens or entire cells will thus reduce immunogenicity and pave the way for an increased stock of implantable materials.

Removal of antigens should be accomplished in such a way as to not disturb the integrity of the collagen matrix. Damage to the matrix decreases the mechanical strength of the implant. Structural alterations in the collagen fibers may also lead to an inability of the graft to be remodelled, revascularized and re-integrated. Early attempts at cellular extraction involving a procedure using a two-phase organic extraction, i.e., chloroform/methanol and hydrochloric acid were successful but severely damaged the underlying collagen matrix. Even when the hydrochloric acid was eliminated and an organic extraction involving chloroform/methanol followed by phosphate buffer was used, the mechanical strength of bovine tendon was found to be 25% of pretreatment levels prior to implantation in a host. After implantation, tissues de-antigenized by this process do regain some mechanical strength.

Another disadvantage of the chloroform/methanol extraction procedure results from disposal of the chloroform waste. Chloroform is toxic and must properly be disposed of. Such disposal is costly, but regardless of cost, will always represent a source of pollution in the earth's ecosystem. Moreover, the use of chloroform is problematic both in the work place and potentially as a contaminant in the processed tissue.

Another method for reducing antigenicity of allografts or xenografts involves glutaraldehyde fixation. Glutaraldehyde fixation is used commercially to prepare bovine heart valves for human implantation. However, such implants are known to retain some antigenicity after implantation. Glutaraldehyde processing is also known to cause an excessive inflammatory response in the surrounding host tissue following implantation. Moreover, the crosslinking resulting from the aldehyde produces a graft that is a permanent implant with little possibility of host cellular infiltration and remodeling.

Consequently, there exits a need to remove cellular debris and reduce antigenicity by less toxic and more efficacious means. A new process is disclosed herein which alleviates or removes the above-described shortcomings in debris and antigen removal from implantable tissue.

SUMMARY OF THE INVENTION

In accordance with the present invention, tendon and ligament cells which include tenoblasts, fibroblasts, and other cells of hematopoietic origin, cellular debris, interstitial ground substance, inflammatory substances, and other antigenic materials are removed from allograft and/or xenograft soft tissues such as tendons or ligaments by use of extraction agents. The extraction agents include permeation enhancers typically having bipolar molecules which can be combined with a polar hydrating medium such as a polyol. The bipolar permeation enhancers have polar and non-polar domains in their molecular structure. Suitable extraction agents include $C_3$–$C_{20}$ fatty acid esters, polyols, monohydric alcohols having three or more carbon atoms, surfactants or mixtures of surfactants which may be cationic, anionic, non-ionic or amphoteric, and aprotic solvents. The antigenic material and/or cellular debris is removed from the allograft or xenograft tissue by contact of the tissue with one or more extraction agents.

Use of extraction agents according to the present invention can reduce or completely eliminate the use of chloroform and its attendant difficulties in the removal of antigens and cellular debris from transplant material. The integrity of the collagen matrix is largely unaffected by contact with the extraction agents.

DETAILED DESCRIPTION OF THE INVENTION

Extraction agents according to the present invention remove cellular debris, interstitial ground substances, antigens, antigen generating materials and other irritants from fibrous connective tissue. The extraction agents described herein may include one or more components which form extraction mixtures. These components include permeation enhancers made of bipolar molecules, i.e., the molecules have both polar and non-polar functionality. Other extraction agents include aprotic solvents, monohydric alcohols having three or more carbon atoms and polyols. As used herein, the designation "$C_n$," wherein C is a carbon atom and n is an arabic numeral, denotes cabon atoms which may appear in a molecule. For example, "$C_3$–$C_{20}$" means that from three to twenty carbon atoms are present.

Permeation enhancers, in accordance with the present invention, include bipolar surface active agents which are ordinarily categorized by their hydrophilic or polar portions and are divided as follows: cationic, anionic, non-ionic and amphoteric. Cationic agents are exemplified by amine salts and quaternary ammonium salts. Common examples of anionic agents are those containing carboxylate, sulfonate and sulfate ions. Non-ionic surfactants are conveniently divided into those that are relatively water insoluble and those that are quite water soluble. The relatively water insoluble non-ionics may include the long chain fatty acids and their water insoluble derivatives including (1) fatty alcohols such a lauryl, cetyl, and stearyl alcohols; (2) glyceryl esters such as the naturally occurring mono- di-, and triglycerides; and (3) fatty acid esters of fatty alcohols and other alcohols such as propylene glycol, polyethylene glycol, and sorbitano to increase the water solubility of these compounds and to form a second group of non-ionic agents, polyoxyethylene groups are added through an ether linkage with one of their alcohol groups. Amphoteric agents exhibit both anionic and cationic properties. The major group of molecules falling into this category are those containing carboxylate or phosphate groups as the anion and amino or quaternary ammonium groups as the cation. The former group is represented by various polypeptides, proteins and the alkyl betaines, while the latter group consist of natural phospholipids such as the lecithins and cephalins. Other extraction agents according to the present invention include aprotic solvents such as dimethylsulfoxide and dimethylformamide. $C_3$–$C_{20}$ fatty acid esters, monohydric alcohols having three or more carbon atoms, and polyols also act as extraction agents in accordance with the present invention and will remove undesirable cellular elements from connective tissue.

Representative examples of extraction agents for purposes of the present invention include but are not limited to monoglycerides, such as glycerol monolaurate; diglycerides; triglycerides; hexamethylene lauramide; dimethyl formamide; propylene glycol; diethyltoluamide; N-methyl-1-2-pyrrolidone; declymethylsulfoxide; benzyl alcohol; dimethyl sulfoxide; alkyl-N-N-dialkyl substituted aminoacetates; lecithin; dimethylacetamide; laurocapram; dodecyl-L-pyroglutamate; 1-oxohydrocarbyl-substituted azacyclohexanes; Triton-X 100; hydromethylacetamide; tetrahydrofurfuryl alcohol; methyl laurate; isopropyl myristate; isopropyl stearate; polyoxyethylene/ polyoxypropylene block copolymers; isopropyl palmitate; sodium dodecyl sulfate; phosphoglycerides and enamines. Individual permeation enhancers having bipolar molecules may be combined with other permeation enhancers to form useful extraction mixtures. Moreover, permeation enhancers having bipolar molecules may be combined with one or more polyols such as propylene glycol or a monohyric alcohol having three or more carbon atoms such as propanol to form other extraction mixtures according to the present invention.

A preferred extraction mixture used in accordance with the instant invention generally involves admixing a surfactant into a polar solvating medium such as a $C_3$–$C_{20}$ fatty acid ester admixed with an alkylene glycol. The concentration $C_3$–$C_{20}$ fatty acid ester may range from about 0.5% to about 80% by weight and the alkylene glycol may range from about 20% to about 99.5% by weight. In a more preferred embodiment, glycerol monolaurate is admixed with propylene glycol to form an extraction mixture which is then placed in contact with the implantable tissue.

In the present novel process of removing cellular debris, antigens, and other irritants, the allograft or xenograft tissue is contacted with one or more extraction agents for from about 0.5 to about 48 hours or more depending upon the thickness of the tissue, but preferably about 8 hours at room temperature under mild agitation. A suitable temperature range of immersion is from about 4° C. to about 37° C. and most preferably, about 23° C. to about 27° C. The tissue is then removed from contact with the extraction agent and rinsed to remove excess extraction agent and remaining cellular debris.

If desired, the allograft or xenograft tissue can be sterilized by ultraviolet radiation by any means known to those with skill in the art. Such irradiation may be accomplished before, during or after treatment with the extraction agent.

The extraction agent may also be combined with one or more other components that are beneficial to the process of preparing implant tissue. Antibiotics, antifungals, antiviral agents, immunosuppressive agents, antiinflammatory agents, growth factors, osteogenic factors, anticoagulants, antihistamines, hormones, enzymes, disinfectants and preservatives can all be suitable. Examples of antibiotics include but are not limited to bacitracin, polymyxin B sulfate, erythromycin, neomycin, penicillin and penicillin derivatives, tetracycline and tetracycline derivatives, chloromycetin, streptomycin, cefazolin, tobramycin and gentamycin, etc. Antifungals include but are not limited to amphotericin B and griseofulvin. Antiviral agents include but are not limited to acyclovir and idoxuridine. Immunosuppressive agents include but are not limited to cyclosporine and cyclophosphamide. Anti-inflammatory agents include but are not limited to indomethacin and naproxen. Growth factors include but are not limited to platelet derived growth factor and insulin-like growth factor. Osteogenic factors include but are not limited to BMP 1 and BMP 2. Anticoagulants include but are not limited to heparin and dicumarol. Antihistamines include but are not limited to diphenhydramine hydrochloride and tripelennamine hydrochloride. Hormones include but are not limited to growth hormone, cortisone acetate and dexamethasone. Enzymes include but are not limited to streptokinase and trypsin. Disinfectants and preservatives may also be present in a suitably effective amount. Examples of disinfectants and preservatives which can be employed include but are not limited to ethylene oxide, propylene oxide, ethanol, hydrogen peroxide (preferably as 3% hydrogen peroxide in aqueous solution), chlorine dioxide, chlorahexidene gluconate, glutaraldehyde, formaldehyde, peracetic acid (hydrogen peroxide and acetic acid in aqueous solution), povidone iodine (polyvinylpyrrolidone), sodium hypochlorite, quaternary ammonium compounds, cetyl alcohol and benzalkonium chloride. Optimum amounts of these and other optional components of the extraction mixture can readily be determined based upon the application contemplated and routine experimentation. It should be noted that bipolar permeation enhancers also manifest a viracidal and bacteriacidal effect in and of themselves.

Extraction agents, in accordance with the present invention, and in addition to removing antigenic substances, also remove other cellular debris and interstitial ground substance from fibrous connective tissue. While certain cellular debris and interstitial ground substances found in the tissue may not possess antigenic potential per se, they can still cause an adverse reaction in a transplant host. Thus, in addition to possible immunogenic reaction, these materials can cause irritation and independent allergic or inflammatory response within the transplant host. Treatment of transplantable tissue with extraction agents will prevent such adverse reaction in the host by removing cellular debris and interstitial ground substance prior to implantation of the tissue.

After contact with the extraction agent, the allograft or xenograft may be washed with distilled water, sterile water, isotonic sodium chloride solutions, or other suitable rinsing solutions such as Ringer's solution or lactated Ringer's solution to remove excess extraction agent, remaining debris, antigenic material and/or other irritants. After rinsing, the tissue may then be frozen, lyophilized and/or implanted.

If desired, an above-described extraction agent or mixture may be further combined with an organic chloroform/methanol extraction solution or with a glutaraldehyde fixation process. Combining extraction agent(s) in accordance with the present invention with a chloroform/methanol solution permits a downward adjustment in the amount of chloroform used which helps alleviate or reduce the problems associated with using chloroform in the workplace.

It is desirable that the mechanical strength of the implantation tissue should be preserved or substantially maintained after removal from the donor. As fibroblasts in the fresh tendon or ligament die, they release collagenase which results in auto-digestion of the collagen matrix. Consequently, prior to treatment with an extraction agent or mixture, the tissue can be harvested and immediately placed in an iced, balanced salt solution to prevent cell death. Then, ethylenediaminetetraacetic acid (EDTA), a potent collagenase inhibitor, is added to the salt solution, and later to the rinse solution after antigen and/or debris removal. A time dependent decrease in mechanical strength of the graft tissue may occur following antigen and/or debris removal and prior to implantation. The problem can be eliminated by freezing or lyophilizing the graft tissue when in storage.

The following examples show the effectiveness of a novel extraction mixture according to the present invention as compared to existing methods of antigen and/or cellular debris removal. The examples described below are not to be construed as limiting, but merely as illustrative of certain aspects of the invention.

EXAMPLE I

The patellar tendons of both legs of three mature (1 year old) New Zealand white rabbits were studied. Five millimeters×ten millimeters×one millimeter samples, cleared free of fascia, were obtained from each of three frozen rabbit specimens for each of five employed treatments. The five treatments consisted of:

1) untreated frozen control;
2) 1 volume methanol: 1 volume chloroform control solution;
3) 1 volume 95% ethanol: 1 volume distilled $H_2O$;
4) 1 volume 95% ethanol: 1 volume distilled $H_2O$: 1 volume Solution A; and 5) undiluted Solution A;

where Solution A contains 2 gms glycerol monolaurate and 100 mls propylene glycol.

One tissue sample from each of the three specimens was immersed into 2 ml of respective treatment solution (with the exception of untreated frozen controls). Samples were incubated in solution for four hours at room temperature with mild shaking on a rocking shaker. To remove excess solution following incubation, samples were transferred into 5 ml distilled $H_2O$, and washed for five minutes with shaking. Samples were then quick-frozen at $-70°$ C. later rethawed, and fixed in 10% neutral buffered formalin.

Gross appearances of samples upon incubation were noted. For histological examination, fixed patellar tendon samples were embedded and frozen sections were made. Longitudinal, sagittal, 10 micron sections were cut at midsubstance through the sample. Sections were stained with hematoxylin and eosin by an automatic staining procedure, and then viewed microscopically. Sections were qualitatively observed using light microscopy. At 40× magnification, distribution of nuclei throughout each section was examined. Each sagittal section was noted in each of the four regions. In order to eliminate bias when counting, identity of samples was left unknown until data collection was complete. The counts from the two peripheral regions were averaged, as were the counts from the two central regions. Ten sections for each animal at each of the five treatments were examined. Counts as indicated above obtained from each of ten sections in a group, were averaged. Counts for all animal specimens were then further averaged. The nuclei/ 40X field at periphery and at center of a given section, at each of the five treatments, is graphically represented in FIG. 1.

As can be seen in FIG. 1, the chloroform/methanol treatment (#2) significantly reduced the number of cell nuclei in the peripheral zone after four hours of treatment (the preferred procedure calls for 36 hours treatment compared to the untreated control (#1)). Treatments 3 and 4 (ethanol: distilled $H_2O$ and ethanol distilled $H_2O$: Solution A respectively) produced no significant changes. After only four hours, treatment 5 (Solution A alone) reduced the nuclei count significantly in both the central and peripheral zones, suggesting higher efficiency than chloroform/methanol. Indeed, the reduction in the central zone further suggests that the present extraction mixtures are more effective in reaching and extracting antigens, antigenic generating material, cellular debris, and other irritants from the interior-most portions of the tissue than any other pre-existing treatment.

EXAMPLE II

Human patellar tendons were studied to compare the biomechanical strength of untreated tissue versus tissue treated with an extraction mixture according to the instant invention. Five human tendon samples were treated as described above in Example I with undiluted solution A. Eight human tendon samples were used as a control for purposes of comparing biomechanical strength of tissue treated with the present extraction mixture and those not so treated. The following parameters were defined for both the treated and control tendons:

1. Cross-sectional area ($mm^2$) of the tissue sample;
2. Cyclic load relaxation (% 10th cycle/1st cycle);
3. Static load relaxation (% initial-finish/initial);
4. Failure load (newtons);
5. Failure stress (megapascals).

More specifically, a central 7 mm section of each patellar tendon was mounted in an Instron 1122 Materials Testing Machine. Both patella and tibial bone ends were cemented in clamps with polymethylmethacylate. A one Newton tensile preload was applied to all specimens to provide a consistent starting position. Multiple cross-sectional area measurements were then taken in the midsubstance region using Vernier calipers. The specimen was then submersed in phosphate buffered saline (PBS, pH 7.2) at 37° C. The one Newton tensile preload was redefined in the PBS. Specimens were then cycled 30 times at 10 mm/min to a fixed displacement of approximately 4% total system strain (based on individual specimen length). On the 31st cycle, the specimen was held at this displacement and remained in this position for 20 minutes before being returned to its preload position. The specimen was then distracted to failure at a crosshead speed of 20 mm/min.

The results of the biomechanical tests were separately averaged for both the extraction mixture treated tendons and control tendons. The results are summarized in Table 1.

TABLE 1

|  | Cross-Sectional Area ($mm^2$) | Cyclic load relaxation (% 10th cycle/ 1st cycle) | Static load relaxation (% initial-finish/ initial) | Failure load (n) | Failure load mPa |
| --- | --- | --- | --- | --- | --- |
| Treated Average | 33 ± 9 | 90.1 ± 2.6 | 23.9 ± 6 | 1129 ± 352 | 35 ± 12 |
| Control Average | 30 ± 7 | 87.3 ± 4.4 | 20.1 ± 12.1 | 1121 ± 318 | 38 ± 9 |

A comparison of the above-results demonstrates that the biomechanical strength of tendons treated with a present novel extraction mixture (Solution A) is not compromised.

It will be understood by those skilled in the art that the foregoing specification is not intended to limit the invention to the embodiments described. On the contrary, it is intended to cover all alternatives, modifications and equivalents within the spirit and scope of the inventive concept.

What is claimed is:

1. A process for removing a material selected from the group consisting of antigens, antigen generating material, tendon cells, ligament cells, cellular debris and inflammatory agents from fibrous tissue comprising contacting the fibrous tissue with at least one extraction agent for a sufficient time to remove said material from the fibrous tissue, wherein the at least one extraction agent includes at least one polyol.

2. A process according to claim 1 wherein the at least one extraction agent further comprises a $C_3$–$C_{20}$ fatty acid ester.

3. A process according to claim 2 wherein the at least one extraction agent comprises a $C_3$–$C_{20}$ fatty acid ester admixed with a polyol.

4. A process according to claim 3 wherein the $C_3$–$C_{20}$ fatty acid ester is selected from the group consisting of monoglycerides, diglycerides and triglycerides.

5. A process according to claim 3 wherein the $C_3$–$C_{20}$ fatty acid ester is glycerol monolaurate.

6. A process according to claim 4 wherein the polyol is an alkylene glycol.

7. A process according to claim 6 wherein the alkylene glycol is propylene glycol.

8. A process according to claim 3 wherein the at least one extraction agent comprises a mixture of glycerol monolaurate and propylene glycol.

9. A process according to claim 2, wherein said process is carried out in a temperature range of from about 4° C. to about 37° C.

10. A process according to claim 3, wherein the concentration of $C_3$–$C_{20}$ fatty acid ester ranges from about 0.5% to about 80% by weight and the concentration of polyol ranges from about 20% to about 99.5% by weight.

11. A process according to claim 10, wherein the concentration of $C_3$–$C_{20}$ fatty acid ester is about 1.9% by weight and the concentration of polyol is about 98.1% by weight.

12. A process according to claim 2, wherein the contact time of the fibrous tissue with the at least one extraction agent is at least about 30 minutes.

13. A process according to claim 12, wherein the contact time of the fibrous tissue with the at least one extraction agent is about 8 hours.

14. A process according to claim 2, wherein the at least one extraction agent is combined with at least one member selected from the group consisting of antibiotics, antifungals, antiviral agents, immunosuppressive agents, anti-inflammatory agents, growth factors, osteogenic factors, anticoagulants, antihistamines, hormones, enzymes, disinfectants and preservatives.

15. A process according to claim 2, wherein the at least one extraction agent is combined with a mixture of chloroform and methanol.

16. A process according to claim 2, further comprising agitation of the fibrous tissue and the at least one extraction agent during contact.

17. A process according to claim 2, further comprising sterilizing the fibrous tissue by exposure to a sterilizing dose of ultraviolet radiation.

18. A process according to claim 2 further comprising rinsing the fibrous tissue with a rinsing solution following contact with the at least one extraction agent.

19. A process according to claim 18, wherein the rinsing solution is selected from the group consisting of distilled water, purified water, sterilized water, sterile isotonic sodium chloride solution, Ringer's solution, lactated Ringer's solution and neutral buffered formalin solution.

20. A process according to claim 2, wherein the fibrous tissue is selected from the group consisting of tendons and ligaments.

21. A process according to claim 2, wherein the fibrous tissue is mammalian tissue.

22. A process according to claim 2, wherein the fibrous tissue is selected from the group consisting of allograft fibrous tissue and xenograft fibrous tissue.

23. A substantially antigen-free implantable fibrous tissue made substantially antigen-free by the process of claim 2.

24. A substantially antigen-free implantable fibrous tissue according to claim 23 wherein the fibrous tissue is selected from the group consisting of tendons and ligaments.

25. A substantially antigen-free implantable fibrous tissue according to claim 24 wherein the tendons and ligaments are mammalian in origin.

26. A substantially antigen-free implantable fibrous tissue according to claim 23 wherein the fibrous tissue is selected from the group consisting of allograft fibrous tissue and xenograft fibrous tissue.

27. An implantable fibrous tissue made substantially free of cellular debris by the process of claim 2.

28. An implantable fibrous tissue according to claim 27 wherein the fibrous tissue is selected from the group consisting of allograft fibrous tissue and xenograft fibrous tissue.

29. An implantable fibrous tissue according to claim 27, wherein the fibrous tissue is mammalian in origin.

\* \* \* \* \*